(12) United States Patent
Racz (10) Patent No.: US 9,131,960 B2
(45) Date of Patent: *Sep. 15, 2015

(54) SAFETY NEURAL INJECTION SYSTEM AND RELATED METHODS

(75) Inventor: Nicholas Sandor Racz, Irving, TX (US)

(73) Assignee: Custom Medical Applications, Farmers Branch, TX (US)

( * ) Notice: Subject to any disclaimer, the term of this patent is extended or adjusted under 35 U.S.C. 154(b) by 1486 days.

This patent is subject to a terminal disclaimer.

(21) Appl. No.: 12/664,626

(22) PCT Filed: Jun. 13, 2008

(86) PCT No.: PCT/US2008/066953
§ 371 (c)(1),
(2), (4) Date: May 28, 2010

(87) PCT Pub. No.: WO2008/157376
PCT Pub. Date: Dec. 24, 2008

(65) Prior Publication Data
US 2010/0249750 A1 Sep. 30, 2010

Related U.S. Application Data

(60) Provisional application No. 60/943,823, filed on Jun. 13, 2007.

(51) Int. Cl.
*A61B 17/34* (2006.01)
*A61B 18/14* (2006.01)

(52) U.S. Cl.
CPC ......... *A61B 17/3478* (2013.01); *A61B 18/1477* (2013.01); *A61B 2018/1425* (2013.01)

(58) Field of Classification Search
CPC ........... A61B 17/3478; A61B 18/1477; A61B 2018/1425; A61B 17/3401; A61B 17/3417; A61B 2017/347; A61B 17/3415; A61B 17/3474; A61B 17/3496; A61B 17/34; A61B 17/3421; A61B 1/018; A61B 2010/045; A61B 25/0606; A61B 5/3291; A61B 25/0068; A61B 25/06
USPC .................... 604/103.05, 164.01, 170.03, 20; 606/116
See application file for complete search history.

(56) References Cited

U.S. PATENT DOCUMENTS

| 2,922,420 A | 1/1960 | Cheng |
| 3,565,074 A | 2/1971 | Foti |

(Continued)

OTHER PUBLICATIONS

James Heavner et al., Sharp Versus Blunt Needle: A Comparative Study of Penetration of Internal Structures and Bleeding in Dogs, Pain Practice, Sep. 2003, 226-231, 3-3.

(Continued)

*Primary Examiner* — Jason Flick
(74) *Attorney, Agent, or Firm* — Ramey & Schwaller, LLP (57) ABSTRACT

A safety neural injection system includes at least a partially hollow cannula having an inside diameter, an outside diameter, a first length, a side port located coaxially along the hollow cannula for fluid communication between the inside and the outside of the hollow cannula, and an open distal end. The safety neural injection system also includes a flexible stylet with a shaped tip. The flexible stylet is capable of being releasably locked in a position within the hollow cannula and extends at least the first length of the hollow cannula. The hollow cannula proximate to the distal end includes a rigid bend so as to facilitate placement of the distal end at the treatment site.

25 Claims, 4 Drawing Sheets

(56) References Cited

U.S. PATENT DOCUMENTS

| | | | |
|---|---|---|---|
| 3,856,009 A | 12/1974 | Winnie | |
| 4,230,123 A | 10/1980 | Hawkins, Jr. | |
| 4,308,875 A | 1/1982 | Young | |
| 4,317,445 A | 3/1982 | Robinson | |
| 4,869,717 A * | 9/1989 | Adair | 604/506 |
| 4,973,313 A | 11/1990 | Katsaros | |
| 4,994,034 A | 2/1991 | Botich | |
| 5,106,376 A | 4/1992 | Mononen | |
| 5,209,728 A * | 5/1993 | Kraus et al. | 604/96.01 |
| 5,242,410 A | 9/1993 | Melker | |
| 5,250,035 A | 10/1993 | Smith | |
| 5,279,555 A | 1/1994 | Lifshey | |
| 5,304,141 A | 4/1994 | Johnson | |
| 5,312,360 A | 5/1994 | Behl | |
| 5,336,191 A | 8/1994 | Davis | |
| 5,338,296 A * | 8/1994 | Dalessandro et al. | 604/103.05 |
| 5,466,225 A | 11/1995 | Davis et al. | |
| 5,480,389 A | 1/1996 | McWha | |
| 5,571,091 A | 11/1996 | Davis | |
| 5,573,519 A | 11/1996 | Zohmann | |
| 5,628,734 A | 5/1997 | Hatfalvi | |
| 5,669,882 A | 9/1997 | Pyles | |
| 5,669,883 A * | 9/1997 | Scarfone et al. | 604/164.11 |
| 5,730,749 A | 3/1998 | Battenfield | |
| 5,800,445 A | 9/1998 | Ratcliff | |
| 5,817,074 A | 10/1998 | Racz | |
| 5,836,914 A | 11/1998 | Houghton | |
| 5,865,806 A | 2/1999 | Howell | |
| 5,871,470 A * | 2/1999 | McWha | 604/158 |
| 6,146,380 A * | 11/2000 | Racz et al. | 606/41 |
| 6,245,044 B1 | 6/2001 | Daw et al. | |
| 6,345,044 B1 | 2/2002 | Edgar, III | |
| 6,387,163 B1 | 5/2002 | Leong | |
| 6,447,477 B2 * | 9/2002 | Burney et al. | 604/93.01 |
| 6,547,769 B2 | 4/2003 | VanTassel et al. | |
| 6,558,353 B2 | 5/2003 | Zohmann | |
| 6,855,132 B2 | 2/2005 | VanTassel | |
| 6,949,087 B2 | 9/2005 | VanTassel | |
| 6,969,373 B2 * | 11/2005 | Schwartz et al. | 604/170.03 |
| 2002/0123723 A1 * | 9/2002 | Sorenson et al. | 604/164.01 |
| 2006/0200191 A1 * | 9/2006 | Zadno-Azizi | 606/200 |
| 2006/0276749 A1 * | 12/2006 | Selmon et al. | 604/164.01 |
| 2008/0243081 A1 * | 10/2008 | Nance et al. | 604/164.03 |

OTHER PUBLICATIONS

Office Action dated Apr. 16, 2014, issued in Canadian Application No. 2,690,806.

* cited by examiner

SAFETY NEURAL INJECTION SYSTEM AND RELATED METHODS

CROSS-REFERENCE TO RELATED APPLICATION

This application is a §371 application claiming benefits of PCT/US2008/066953, filed Jun. 13, 2008, which claims priority to U.S. Provisional Application No. 60/943,823, filed Jun. 13, 2007.

FIELD OF INVENTION

The present invention generally relates to safety neural injection systems and related methods of use.

BACKGROUND OF THE INVENTION

Needles and needle systems are used extensively in a wide variety of procedures which are performed in various fields of medicine, such as cardiology, radiology, urology, interventional pain management, and internal medicine. The use of needles and needle systems in invasive procedures in various medical fields has become routine due, in part, to the ability of needles to pass through most tissues without causing significant destruction to the tissues. Conventional hypodermic needles are usually used in conjunction with various types of disposable hypodermic syringes in a number of diagnostic and therapeutic procedures, such as aspiration, blood draws, and biopsies. Another widely-used type of needle system includes a system that employs a catheter and guide member. Such needle systems generally include a small guide member (e.g., guide wire) which is used to guide a larger hollow catheter to a target area (e.g., a vessel, body cavity, tissue, or organ) within a human or animal body. Such needle systems are efficient for both therapeutic and diagnostic purposes Needles with a blocked tip (distal end) and with a side opening are used for procedures such as thoracentesis, which involves inserting the needle through the thoracic cage into the pleural space between the lung and the chest wall to draw off fluid for diagnostic or therapeutic purposes. Thoracentesis needles generally consist of an orifice free, sharp conical end and a circular side hole for draining fluid. However, it is desired in some procedures to have a needle with both an open distal end as well as at least one side opening for the administration of therapeutic, diagnostic or prophylactic agents in multiple directions.

It is also desirable to reduce a risk of internal injury from a sharp blade or edge of a traditional injection system or by providing a leading edge that is at least not as sharp, if not smooth, rounded, or flat. The leading edge may also be made of a material that is more yielding if a dense surface is encountered.

SUMMARY OF THE INVENTION

The summary of the invention is not intended to represent each embodiment or every aspect of the present invention.

Provided herein is a safety neural injection system includes at least a partially hollow cannula having an inside diameter, an outside diameter, a first length, a side port located coaxially along the hollow cannula in fluid communication between the inside and the outside of the hollow cannula, and an open distal end in fluid communication with the inside and outside of the hollow cannula. The safety neural injection system also includes a flexible stylet with a shaped tip. The flexible stylet is capable of being releasably locked in a position within the hollow cannula and extends at least the first length of the hollow cannula. The hollow cannula proximate to the distal end includes a rigid bend so as to facilitate placement of the distal end at the treatment site.

A method of treatment for an individual in need thereof comprising locating a target site of treatment in the individual; adjusting the safety neural injection system described above; such that the system is positioned relative to the individual at the site and orientation; inserting at the target site at least a portion of the safety neural injection system; maneuvering the safety neural injection system inside the individual using the rigid bend proximate to the distal end to facilitate placement of the safety neural injection system at the target site; and treating the individual is also provided herein.

Additionally disclosed is an injection system comprising means for locating a target site for treatment in an individual in need thereof; means for adjusting the safety neural injection system described above; such that said system is positioned relative to said individual at said site and orientation; means for inserting into the individual at least a portion of the safety neural injection described above; wherein the hollow cannula, of the safety neural injection, proximate to the distal end includes a rigid bend so as to facilitate placement of the distal end at the target site; means for maneuvering the distal end of the safety neural injection system inside the individual proximate to the site; and means for treating the individual.

Further, disclosed is a kit comprising the safety neural injection system described above and an agent to be injected, wherein the agent is selected from a group consisting of a therapeutic agent, a diagnostic agent, or a prophylactic agent.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE FIGURES

The foregoing summary as well as the following detailed description of the preferred embodiment of the invention will be better understood when read in conjunction with the appended drawings. It should be understood, however, that the invention is not limited to the precise arrangements and instrumentalities shown herein. The components in the drawings are not necessarily to scale, emphasis instead being placed upon clearly illustrating the principles of the present invention. Moreover, in the drawings, like reference numerals designate corresponding parts throughout the several views.

The invention may take physical form in certain parts and arrangement of parts. For a more complete understanding of the present invention, and the advantages thereof, reference is now made to the following descriptions taken in conjunction with the accompanying drawings, in which.

DETAILED DESCRIPTION OF THE INVENTION

The principles of the present invention and their advantages are best understood by referring to FIGS. 1-4 of the drawings, like numerals being used for like and corresponding parts of the various drawings.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

In the following descriptions and examples, specific details are set forth such as specific quantities, sizes, etc., to provide a thorough understanding of the present invention. However, it will be obvious to those skilled in the art that the present invention may be practiced without such specific details. In many cases, details concerning such considerations and the like have been omitted inasmuch as such details are not necessary to obtain a complete understanding of the present invention and are within the skills of persons of ordinary skill in the relevant art. It is therefore contemplated that the claims will cover any such modifications or embodiments that fall within the true scope of the invention.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition.

The term "attached," or any conjugation thereof describes and refers the at least partial connection of two items.

Exemplary, non-limiting embodiments of medical instrument, neural injection systems, and the like that can be modified according to various teachings include, but are not limited to, U.S. Pat. No. 6,949,087; U.S. Pat. No. 6,855,132; U.S. Pat. No. 6,558,353; U.S. Pat. No. 6,547,769; U.S. Pat. No. 6,387,163; U.S. Pat. No. 6,245,044; U.S. Pat. No. 5,871,470; U.S. Pat. No. 5,865,806; U.S. Pat. No. 5,836,914; U.S. Pat. No. 5,817,074; U.S. Pat. No. 5,800,445; U.S. Pat. No. 5,730,749; U.S. Pat. No. 5,669,882; U.S. Pat. No. 5,628,734; U.S. Pat. No. 5,573,519; U.S. Pat. No. 5,571,091; U.S. Pat. No. 5,480,389; U.S. Pat. No. 5,466,225; U.S. Pat. No. 5,336,191; U.S. Pat. No. 5,312,360; U.S. Pat. No. 5,304,141; U.S. Pat. No. 5,250,035; U.S. Pat. No. 5,242,410; U.S. Pat. No. 5,106,376; U.S. Pat. No. 4,994,034; U.S. Pat. No. 4,973,313; U.S. Pat. No. 4,629,450; U.S. Pat. No. 4,317,445; U.S. Pat. No. 4,308,875; U.S. Pat. No. 4,230,123; U.S. Pat. No. 3,856,009; U.S. Pat. No. 3,565,074; and, U.S. Pat. No. 2,922,420, the contents of which are hereby incorporated by reference as if they were presented herein in their entirety. In general, any catheter may be used with the various embodiments of the present invention.

A "fluid" is a continuous, amorphous substance whose molecules move freely past one another and that has the tendency to assume the shape of its container, for example, a liquid or a gas.

Any agent that can be injected through a needle can be delivered using the inventive method. Typical agents might include drugs, small molecules, pharmaceutical agents, diagnostic agents, biological molecules, proteins, peptides, antibodies, polynucleotides, RNA, DNA, viruses, cells, and combinations thereof. Agents may range in size from small organic molecules to macromolecules such as DNA to intact cells. The agent to be delivered to the injection site may be therapeutic (e.g., chemotherapeutic drug, antibiotic), prophylactic (e.g., vaccine), or diagnostic (e.g., contrast agent for magnetic resonance imaging, labeled metabolite).

Therapeutic agents include any compound useful in the treatment or prevention of a disease. In a particularly preferred embodiment, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, p-adrenergic blocking agent, diuretic, cardiovascular active agent, vasoactive agent, non-steroidal anti-inflammatory agent, nutritional agent, etc. A combination of therapeutic agents may be used in the present invention. The therapeutic agent may also be delivered in various forms, for example, the drug may be encapsulated, or the drug may be in a time release form.

Therapeutic prophalytic or diagnostic agents to be delivered may also include biological molecules such as proteins, peptides, polynucleotides, and oligonucleotides. Examples of proteins or peptides include insulin, cytokines, growth factors, erythropoeitin, antibodies, antibody fragments, etc. Polynucleotides may be delivered for gene therapy and antisense therapy.

In addition to drugs, small molecules, and biological molecules, the invention may be used to deliver viruses and cells. Particularly preferred viruses and cells are those that are therapeutic. Viruses with altered genomes may be used in gene therapy as vectors to introduce a foreign gene into the patient's cells.

Further, agents used for delivery with the inventive method disclosed herein may also include cells. Any type of cell or mixture of cells may be transplanted using the inventive method.

The term "medicament(s)" means and refers to all types of fluidic substances that have a beneficial, desired or therapeutic effect. Non-limiting examples of medicaments suitable for use in the invention methods include anesthesia, biologically active agents, such as small molecule drugs, proteinaceous substances, polynucleotides or nucleic acids (e.g., heterologous DNA, or RNA) and vectors, liposomes, and the like, containing such nucleic acids or polynucleotides, as well as liquid preparations or formulations thereof.

The term "medical instrument" means and refers to any item, instrument or structure capable of connecting to a catheter, such as, but not limited to a stimulation device, tubing, piping, a medicament delivery system, a meter, a liquid repository (e.g., an I.V. bag), a syringe, or the like.

The term "normal insertion procedure" means and refers to a typical surgical or insertion procedure as disclosed in Heavner et al., "Sharp Versus Blunt Needle: A Comparative Study of Penetration of Internal Structures and Bleeding in Dogs", 2003, World Institute of Pain, Pain Practice, 3:3, 226-231.

The term "stylet" means and refers to a small poniard. Stylets of the preset invention are capable of being hollow, but such is not required.

Other than in the operating examples, or where otherwise indicated, all numbers expressing quantities of ingredients or reaction conditions used herein are to be understood as modified in all instances by the term "about".

Various embodiments comprise a safety neural injection and treatment systems and related methods with at least one benefit of enhanced injection characteristics, increased operational efficiency, reduced cost per unit, reduced incidence of injury through intraneural or intravascular injection, reduced incidence of injury through pricking or piercing, or the like.

Various embodiments comprise a safety neural injection system include an at least partially hollow cannula. The cannula is defined by a first inside diameter, a first outside diameter, a first length, a side port located coaxially along the cannula for fluid communication between the inside and the outside of the hollow cannula, and an open distal end. The system also includes a flexible stylet with a shaped tip, wherein the flexible stylet is capable of being releasably locked in a first position within the hollow cannula and extends at least the first length of the hollow cannula. The hollow cannula is proximate to the distal end includes a rigid bend so as to facilitate placement of the distal end near a target region during system administration.

Various embodiments also includes methods and devices that are designed for injection of minute amounts of a fluid therapeutic, diagnostic or a prophylactic agent into tissue or a body wall, for example, an interior body wall. Additionally, the target site is located at sites or organs located in the human digestive system, the circulatory system, nervous system, muscular system, skeletal system, respiratory system, urinary system, reproductive system, excretory system, endocrine system, immune system of the human body is envisioned using the present invention. The amount of the agent to be administered according to the invention method will vary depending upon the goal to be accomplished, the size and age of the subject, the pharmacokinetics of the injectate, and the like.

Various embodiments are designed for treatment of a target tissue(s) at a target site. In an embodiment, treatment of a tissue may be at least one of probing, ablation, stimulating, or the like. In general, treatments capable with various embodiments can be any treatment common in the art and should not be limited by the present disclosure.

A cannula associated with various embodiments may be a cylindrical structure extending from a proximal end to a distal end. The length from the proximate end to the distal end, traveling along the length of the cannula is known as the first length. In various embodiments where a bend in the cannula exists, the first length may be longer than the linear distance from the proximate end to the distal end. In an embodiment, the cannula is of a generally constant circumference. The cannula is capable of being differentiated by an inside diameter and an outside diameter. In an embodiment, an outside diameter is between about 0.0355 to about 0.03600 mm and an inside diameter is between about 0.0230 to about 0.0245 mm. In an alternate embodiment, an outside diameter between about 0.0205 to 0.280 mm and an inside diameter between about 0.0155 to 0.0170 mm. In various embodiments, an inside diameter and an outside diameter are capable of being any desired length and any particular length should not be construed as a limitation on the scope of the appended claims.

In various embodiments, a shaped tip end or distal end of the at least partially hollow cannula may take various shapes. In an embodiment, the distal tip may be the traditional beveled angular plane shape. In another embodiment, the distal tip may be squared with the perpendicular of the lengthwise plane of the cannula. In another embodiment, the distal tip may be a partial bevel, wherein the leading portion of the shaped tip is of a traditional bevel form and the remainder of the tip is formed in a non-beveled shape, such as a stair step. A variety of shapes may be considered for use to achieve the desired results while still possessing an open end.

In various embodiments, a connector may be about the proximal end of the cannula. A connector may be used as an attachment means for attaching the cannula and an optional further medical instrument. The connection or connections at the connector end may be any type of connection common in the art, such, as for example, and not by way of limitation, a luer lock connector, a threaded attachment, an interference fit attachment, a clamp, a system utilizing a dowel, two or more of the aforesaid in combination, or the like.

A flexible stylet of various embodiments may extend through at least a portion of the hollow portion of the cannula. In some embodiments, a stylet may be characterized by an outside diameter and a length extending at least from a proximal end to the distal end, representing the first length. The outside diameter, in various embodiments, is smaller than the first inside diameter of the cannula. In various embodiments, the stylet may be of a length that is longer than the first length. In some embodiments, the stylet comprises a side port an is at least partially hollow. In an embodiment, the stylet and the cannula define a passageway for passage of at least one medicament.

In various embodiments, the material of construction may permit the flexible stylet so as to bend within the hollow cannula to conform generally to its internal shape. In some embodiments, the material of construction of the flexible stylet may be of a polymer material. In some embodiments, the material will be made of a biocompatible material. Examples of such embodiments include materials such as polyethylene, polypropylene, and polyfluorocarbons. In some alternative embodiments, the material of construction may be of a metallic material. Examples of embodiments include steel alloys, titanium alloys, and aluminum. In various embodiments, the stylet exhibits elastic deformation in regards to insertion and removal from the cannula.

In various embodiments, the flexible stylet may be capable of being inserted into the cannula so that the distal tip of the stylet may be position within the cannula at any point. In an embodiment, the distal end of the stylet may be positioned so that the distal end of the stylet is equivalent with the distal end of the cannula in relation to the proximate end of the cannula. In an alternate embodiment, the distal end of the stylet may extend past the distal end of the cannula. In an alternate embodiment, the distal end of the cannula may extend past the distal end of the stylet.

In various embodiments, the flexible stylet may possess a shaped distal tip to support not only the "safety" function of providing a smooth, flat, or leading surface versus the potentially sharp or rigid edge of the distal tip of the hollow cannula but also provide the means for the leading tip of the system to be later retracted when the flexible stylet is partially or completely decoupled from the hollow cannula so as to retract the shaped tip of the flexible stylet from its leading position. In some embodiments, the shaped tip may be rounded, similar to a half-dome or a bullet. In some embodiments, the shaped tip may be flat in a manner that is squared with the length of the stylet. In some embodiments, the shaped tip may be a traditional bevel angle. In some embodiments, the shape of the tip will conform approximately to the shape of the distal end of the cannula. In some embodiments, the shaped end of the flexible stylet may be formed in a manner so as to form a flush and flat surface with the distal end of the cannula. In some embodiments, the shaped tip may be edged or pointed such that at least a portion of the distal edge of the stylet is capable of penetrating a tissue that a normal insertion procedure could not penetrate. In some embodiments, the shaped tip of the stylet is a point.

Various embodiments may fixedly connect, releasably connect, or leave unconnected the flexible stylet and the cannula. In another embodiment, the stylet is capable of sliding within the cannula. In another embodiment, the stylet is releasably secured within the cannula by a locking mechanism, such as, but not limited to a luer lock, an interference fit, a snap, screw threads, or the like. In an embodiment of a luer lock system, internal male luer threads are located in or about the stylet adjacent to receive and engage a cannula having female luer threads thereon. In other embodiments, the luer lock is reversed. In another embodiment, the cannula is welded to or otherwise fixedly connected to the cannula.

A side port in various embodiments may be a port extending from the exterior of the hollow cannula to the interior of the hollow cannula or the flexible stylet. The shape of the side port may vary. In an embodiment, a port may be circular. In another embodiment, a port may be ovular. In an another embodiment, a port may be a quadrangular port, such as a rectangle or a square. In an another embodiment, the port is triangular. It can be seen by one skilled in the art that the shape of the port may be formed in any shape sufficient to permit fluid aspiration.

A side port in various embodiments may be further characterized by the associated edge of the port on the cannula or stylet. In an embodiment, a port may have a slightly inwardly beveled edge extending from the exterior surface of the hollow cannula to the interior surface. In an alternate embodiment, a port may have a slightly outwardly beveled edge extending from the interior surface of the hollow cannula to the exterior surface. In an embodiment, the degree of bevel may be used to change the pressure of the medicament as it enters the target tissue; facilitate a change in the degree of spread of the medicament; and, allow for a smooth surface as the cannula is inserted to the target tissue.

Further embodiments may comprise a cannula or stylet with multiple ports arranged in any orientation about the shaft. In an embodiment, a stylet may comprise, in application, a side port across a cannula and a side port across the stylet. In various embodiments, the side ports may be positioned such that reasonable alignment of the side ports occurs at a desired position of the stylet within the cannula such that a medicament may pass from across the reasonably aligned side ports.

Various embodiments may include a wire or other means of conveying stimulation to a target tissue. In an embodiment, the wire may extends along the cannula from about the proximal end to about the distal end of the distal tip. In another embodiment, the wire may be integral (attached to) with the cannula. In another embodiment, the wire may extend along the outside of the cannula. In another embodiment, a wire may extend along, through, or is integral with the stylet.

Design consideration that may be implemented with various embodiments include, but are not limited, to designing the wire and connector such that they may be utilized as a "plug and use" type of arrangement. A plug and use arrangement is beneficial because it reduces the complexity of the device and reduces loose wires. In an embodiment, the wire may be formed into the connector such that when the connector is connected to another medical instrument, the wire is able to communicate with the instrument. However, any connection common in the art that would allow the wire to communicate with a medical instrument may be contemplated within various embodiments.

Various embodiments may include insulation or at least one form insulation about the cannula, stylet, or wire. As may be appreciated by one of ordinary skill in the art, any material of construction that provides electrical or thermal insulation could be used such as, but not limited to, a plastic, a rubber, a metal, a non-metal, or the like. In some embodiments, the insulation covers the exterior of the hollow cannula along the entire first length. In some embodiments, the insulation covers the exterior of the hollow cannula until it reaches the rigid bend portion of the hollow cannula. In some embodiments, the insulation covers an exterior portion of the hollow cannula in between the hub and the rigid bend portion.

Various embodiments may include insulation around the hollow cannula, flexible stylet, or wire that is constructed of a material that permits differentiation between the insulation and the hollow cannula or flexible stylet material during real-time procedural use. Numerous procedures, such as, but not limited to, fluoroscopic guidance procedures, NMR procedures, X-ray procedures, direct viewing procedures, or the like, may be used during a medical procedure to determine the position of a safety neural injection system and the target location. In such embodiments, a practitioner may choose an embodiment with an insulation coating wherein the absorptive or reflective difference between the insulation coating and the uninsulated portion of the safety neural injection system can be differentiated in real-time using the selected real-time viewing system. For example, a particular insulation may absorb the energy from a real-time viewing system and show up as a dark segment whereas the uninsulated portion may reflect the energy and appear to be a bright segment. In such embodiments, the differentiation in reflectivity and absorption may provide a method to determine the exact position of the shaped tip, the distal tip, or the side portal of the safety neural needle in relation to the treatment site, given that the relative distance from the insulation/non-insulation border.

Further modifications of embodiments of a neural injection system with a wire comprise the introduction of a probe about the shaft or wire. Various probes capable of use with embodiments include temperature probes, stimulation probes, cameras, or the like.

Various embodiments may include methods of use of a safety neural injection system. An embodiment of a method may include locating a site for treatment in a patient; inserting into a patient at least a portion of a safety neural injection system comprised of an at least partially hollow cannula being defined by a first inside diameter, a first outside diameter, a first length, a side port located coaxially along the hollow cannula for fluid communication between the inside and the outside of the hollow cannula, and an open distal end; a flexible stylet with a shaped tip, wherein the flexible stylet is capable of being releasably locked in a first position within the hollow cannula and extends at least the first length of the hollow cannula; wherein the hollow cannula proximate to the distal end includes a rigid bend so as to facilitate placement of the distal end at the treatment site, maneuvering the distal end of the safety neural injection system inside a patient proximate to the site; and treating the patient.

Further embodiments of a method may include stimulating a tissue. Further embodiments of a method may include ablating at least a portion of the tissue about a site. Other embodiments comprise probing a tissue. And yet further embodiments of a method may include preparing a patient for administering a medicament.

In an embodiment of an administration of a block, such as a nerve block, the method may comprise preparing the patient. In an embodiment, preparing the patient may comprise placing a patient in a supine position or extended position, without a pillow, with the patient's head in a neutral position.

In an embodiment of administration of a medicament, while standing on side of the body that is to be blocked, the physician may tactilely locates the cricoid cartilage. In such an embodiment, the neural injection system may be inserted in a position approximately one finger breadth below the cricoid cartilage, between the carotid sheath and the trachea on the side to be blocked, while aiming slightly medially until bony contact is made with the ventral lateral side of the body of the seventh cervical vertebra. When the neural injection system is in said position, the anesthesia may be injected.

In another embodiment, there may be methods for injecting a medicament into tissue of a subject. The method may include inserting the distal portion of an embodiment into the tissue of the subject and causing a therapeutic amount of medicament to enter multidirectionally from a distal end into the tissue.

Figure 1:
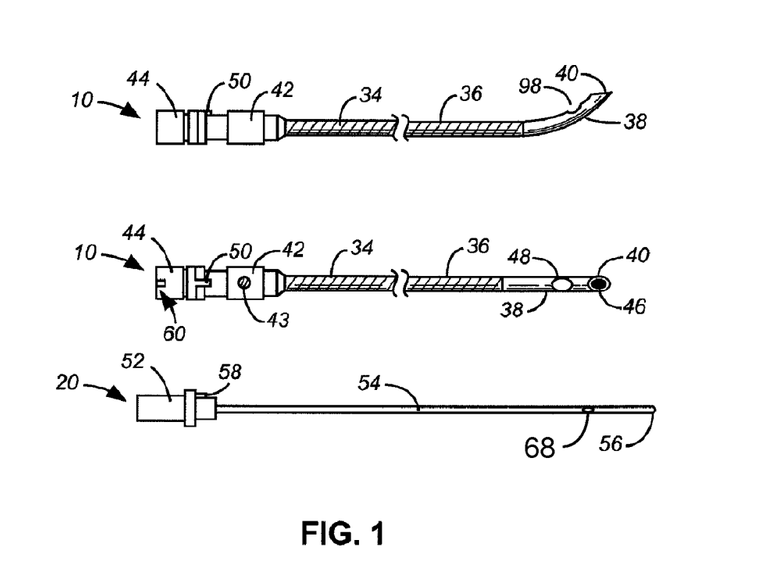
FIG. 1 is an illustration of an embodiment of a safety neural injection system in a disassociated perspective.

FIG. 1 illustrates an embodiment of a safety neural injection system 1 with a cannula 10 (viewed in both top and side perspectives) and a mating flexible stylet 20 in a disassociated manner. The cannula 10 is capable of being characterized as having a first length measured from the proximate end of the stylet mating hub 44 to the distal opening 46 of the distal tip 40. In this embodiment, the cannula 10 has a hollow cannula shaft 34 with a rigid bent portion 38 near the distal end and possesses insulation 36 lining part of the cannula shaft 34. Insulation 36 is capable of use to isolate a radio frequency (RF) portion of the cannula, to isolate an RF wire, and/or the like. However, various embodiments comprise a cannula without insulation.

In an embodiment, a side port 48 is located in the rigid bent portion 38 of the hollow cannula shaft 34 proximate to the distal tip 40 and distal opening 46. However, a side port is not present in various other embodiments. At the proximate end of the cannula 10, a hub 42 is endowed with a index mark 43 to visually inform the user of the direction of bend the rigid bent portion 38 is directed toward. Additionally, an index notch 50, located on the stylet mating hub 44, performs a similar function tactilely so as to inform the user of the directional perspective of the rigid bent portion 38. The stylet mating hub 44 also possesses a stylet receiving notch 60 so as to fixedly engage a flexible stylet 20 and directionally fix its position.

In this embodiment, the flexible stylet 20 is comprised of a stylet hub 52 with a stylet lock notch 58 shaped to mate with the stylet receiving notch 60 in a frictional manner, a stylet shaft 54, a shaped stylet tip 56, and a stylet side port 68. The stylet shaft 54 is characterized by having a length of at least the first length associated with the first length of the cannula 10. The stylet shaft is also characterized by a material of construction that permits elastic return even after prolonged engagement within a hollow cannula 10 with a rigid bent portion 38.

Figure 2:
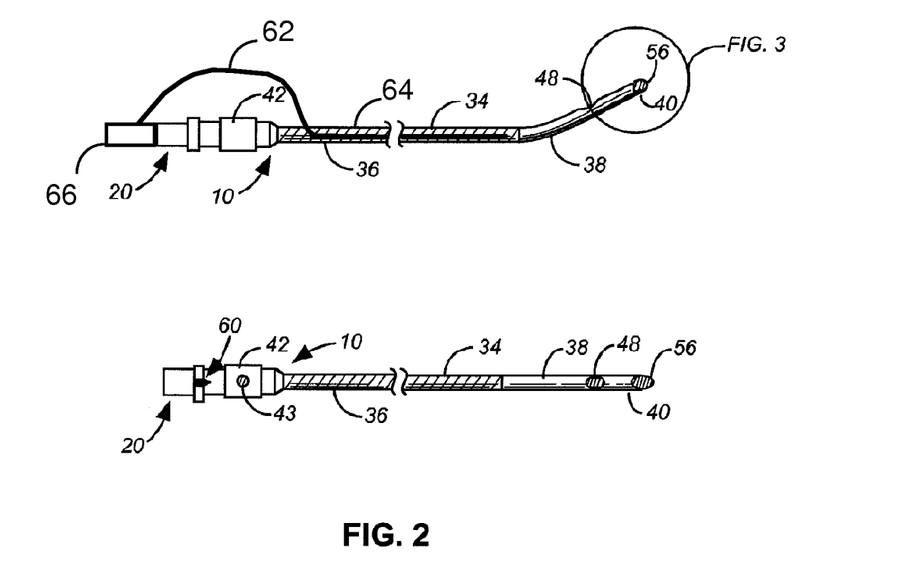
FIG. 2 is an illustration of an embodiment of a safety neural injection system in an associated perspective.
Figure 3:
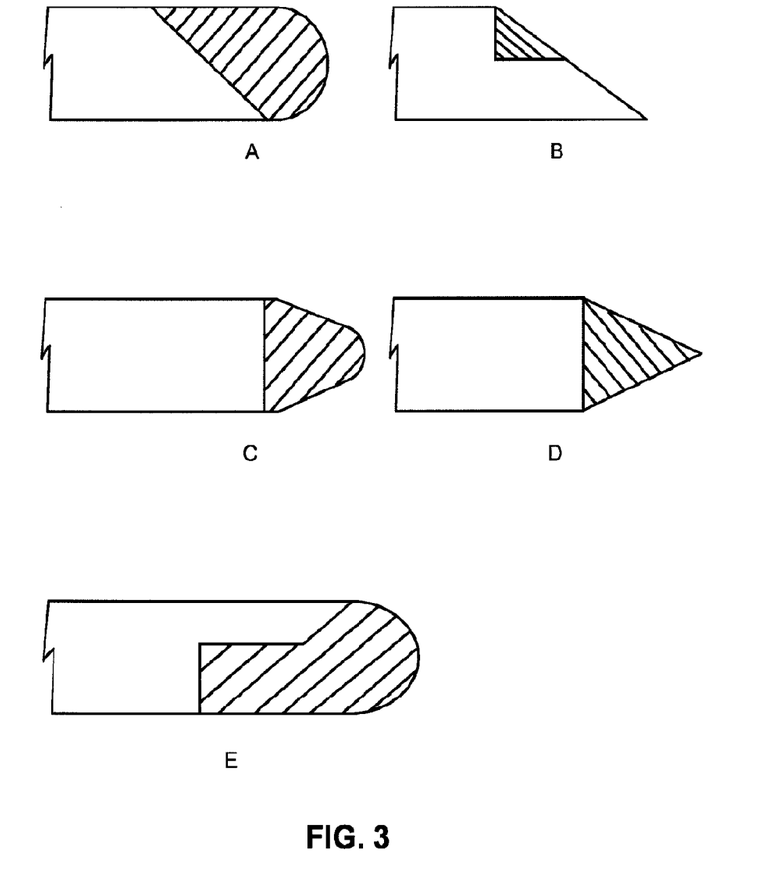
FIGS. 3A-3E are illustrations of embodiments of distal tips of hollow cannulas associated with shaped tips of flexible stylets; and, FIG. 4 is an illustration of an alternate embodiment of a safety neural injection system in a disassociated perspective.

FIG. 2 illustrates another embodiment of a safety needle injection system wherein the flexible stylet 20 that extends beyond the first length of the cannula 10 possessing a shaped tip 56 is mated and engaged with a cannula 10 with a side port 48, a distal tip 40, a rigid bent portion 38, a wire 62, a probe 64, and insulation 36. The wire is attached to connector 66.

FIGS. 3A-3E illustrates more closely several embodiments of the distal tip 40 of the cannula 10 with the shaped tip 56 of the flexible stylet 20. FIG. 3A shows an example of a shaped tip 56 as a rounded end extending beyond the end of the traditional bevel shape of the distal tip 40. FIG. 3A also inherently demonstrates a flexible stylet 20 that has a stylet shaft 54 that is longer than the first length of the associated cannula 10 because the end of the flexible stylet 20 extends beyond the furthest distal point of the distal tip 40. FIG. 3B shows an example of a partial bevel distal tip 56 at the distal end of a cannula 10 matched with tip of a flexible stylet 20, wherein the shape of the shaped tip 56 corresponds with the angle of the bevel portion of the distal tip 56 and forms a partially flush and flat surface at the open distal end 40. Such a combination of shapes that form a flush, beveled surface might be intended for use to prevent tearing and "grabbing" of the distal tip on parts of the body by the more squared portion of the distal tip 40. FIGS. 3C and 3D show a distal tip 40 in a squared form with flexible stylet shaped tips 56 extending beyond the first length. FIG. 3C gives an example of a rounded point or "pen point" form for shaped tip 56. FIG. 3D gives an example of a sharp leading point for shaped tip 56. FIG. 3E is an illustration of the needle tip disclosed in U.S. Pat. No. 5,810,788, the contents of which are hereby incorporated by reference.

Figure 4:
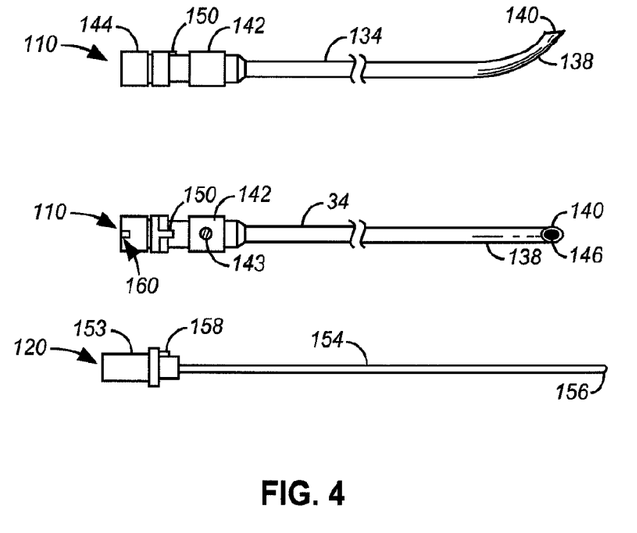

FIG. 4 illustrates an alternate embodiment of a safety neural injection system with a cannula 110 (viewed in both top and side perspectives) and a mating flexible stylet 120 in a disassociated manner. The cannula 110 is capable of being characterized as having a first length measured from the proximate end of the stylet mating hub 144 to the distal opening 146 of the distal tip 140. In this embodiment, the cannula 110 has a hollow cannula shaft 134 with a rigid bent portion 138 near the distal end.

The proximate end of the cannula 110, a hub 142 is endowed with a index mark 143 to visually inform the user of the direction of bend the rigid bent portion 138 is directed toward. Additionally, an index notch 150, located on the stylet mating hub 144, performs a similar function tactilely so as to inform the user of the directional perspective of the rigid bent portion 138. The stylet mating hub 144 also possesses a stylet receiving notch 160 so as to fixedly engage a flexible stylet 120 and directionally fix its position.

In this embodiment, the flexible stylet 120 is comprised of a stylet hub 152 with a stylet lock notch 58 shaped to mate with the stylet receiving notch 160 in a frictional manner, a stylet shaft 154, and a shaped stylet tip 156. The stylet shaft 154 is characterized by having a length of at least the first length associated with the first length of the cannula 110. The stylet shaft is also characterized by a material of construction that permits elastic return even after prolonged engagement within a hollow cannula 110 with a rigid bent portion 138.

As such, various embodiments comprise a safety neural injection system comprising an at least partially hollow cannula being defined by a first inside diameter, a first outside diameter, a first length, and an open distal end in fluid communication with the inside and outside of the hollow cannula; a side port located coaxially along the hollow cannula in fluid communication between the inside and the outside of the hollow cannula; and a flexible stylet with a shaped tip, wherein the flexible stylet is capable of being releasably locked in a first position within the hollow cannula and extends at least the first length of the hollow cannula; wherein the hollow cannula proximate to the distal end includes a rigid bend so as to facilitate placement of the distal end at a target site. Further embodiments are characterized by the first position of the shaped tip of the flexible stylet being in a flush position relative to the open distal end of the hollow cannula. Further embodiments comprise a side port. In various further embodiments, the stylet is retractable. Further embodiments comprise a kit comprising the safety neural injection system of as herein described and an agent to be injected.

Further embodiments comprise a method of treatment for an individual in need thereof comprising locating a target site of treatment in the individual; adjusting the safety neural injection system of claim 1; such that said system is positioned relative to said individual at said site and orientation; inserting at the target site at least a portion of said safety neural injection system; maneuvering the safety neural injection system inside said individual using the rigid bend proximate to the distal end to facilitate placement of said safety neural injection system at said target site; and treating said individual.

Various further embodiments comprise an injection system comprising means for locating a target site for treatment in an individual in need thereof; means for adjusting the safety neural injection system as herein described; such that said system is positioned relative to said individual at said site and orientation; means for inserting into the individual at least a portion of the safety neural injection system as herein described, wherein the hollow cannula, of the safety neural injection system as herein described, proximate to the distal end includes a rigid bend so as to facilitate placement of the distal end at the target site; means for maneuvering the distal end of the safety neural injection system inside said individual proximate to the site; and means for treating the individual.

Although the present invention is described with several embodiments, various changes and modifications may be suggested to one skilled in the art. In particular, the present invention is described with reference to certain polymers and materials and methods of processing those materials, but may apply to other types of processing or materials with little alteration and similar results. Furthermore, the present invention contemplates several process steps that may be performed in the sequence described or in an alternative sequence without departing from the scope and the spirit of the present invention. The present invention is intended to encompass such changes and modifications as they fall within the scope and the spirit of the appended claims.

What is claimed is:

1. A safety neural injection system comprising: an at least partially hollow cannula being defined by a first inside diameter, a first outside diameter, a first length, and an open distal end in fluid communication with the inside and outside of the hollow cannula; a side port located coaxially along the hollow cannula in fluid communication between the inside and the outside of the hollow cannula; and a flexible stylet with a shaped tip, wherein the flexible stylet is releasably locked in a first position within the hollow cannula and extends at least the first length of the hollow cannula; wherein the hollow cannula proximate to the distal end includes a rigid bend so as to facilitate placement of the distal end at a target site.

2. The system of claim 1, wherein the first position is characterized by the shaped tip of the flexible stylet being in a flush position relative to the open distal end of the hollow cannula.

3. The system of claim 1, wherein the shaped tip is configured so as to form a flat plane across the open distal end.

4. The system of claim 1, wherein the first position is characterized by the shaped tip of the flexible stylet protruding beyond the first length.

5. The system of claim 1, further comprising an agent selected from the group consisting of a therapeutic agent, a diagnostic agent and a prophylactic agent.

6. The system of claim 5, wherein said therapeutic agent is anesthesia.

7. The system of claim 1, further comprising a connector.

8. The system of claim 1, further comprising a wire.

9. The system of claim 1, further comprising an insulation.

10. The system of claim 1, further comprising a probe.

11. The system of claim 7, further comprising a wire, wherein the wire is connected about the connector with an instrument.

12. The system of claim 11, wherein said connector is a plug and use connector.

13. The system of claim 1, wherein the stylet further comprises a side port.

14. The system of claim 1, wherein the stylet is retractable.

15. A method for the administration of an agent with the safety neural injection system of claim 1 comprising: locating a target site for administration; adjusting the safety neural injection system; such that said system is positioned relative to said site; inserting at the target site at least a portion of said safety neural injection system; maneuvering the safety neural injection system using the rigid bend proximate to the distal end to facilitate placement of said safety neural injection system at said target site; and administering said agent.

16. The method of claim 15, wherein the agent is selected from the group consisting of a therapeutic agent, a diagnostic agent and a prophylactic agent.

17. The method of claim 15, wherein the therapeutic agent is anesthesia.

18. The method of claim 15, wherein the agent is used for stimulating a tissue about the site.

19. The method of claim 15, wherein said agent is injected through a biopsy needle.

20. The method of claim 18, wherein stimulating the tissue comprises ablating at least a portion of the tissue.

21. The method of claim 15, wherein the step of maneuvering the distal end is performed using a real-time imaging device.

22. The method of claim 15, wherein interaction between the safety neural injection system and a real-time imaging device permits a user to determine the exact location of the distal end at the target site.

23. The method of claim 15, wherein said target site is a site selected from a group consisting of the digestive system, the circulatory system, nervous system, muscular system, skeletal system, respiratory system, urinary system, reproductive system, excretory system, endocrine system, and immune system of the human body.

24. A kit comprising the safety neural injection system of claim 1 and an agent to be administered.

25. The kit of claim 24, wherein said agent is selected from a group consisting of a therapeutic agent, a diagnostic agent and a prophylactic agent.

* * * * *